United States Patent
Geen et al.

(10) Patent No.: US 6,187,922 B1
(45) Date of Patent: *Feb. 13, 2001

(54) PROCESS FOR THE PREPARATION OF PURINE DERIVATIVES

(75) Inventors: Graham Richard Geen, Dunmow; Richard Lewis Jarvest, Ware, both of (GB)

(73) Assignee: SmithKline Beecham plc, Brentford (GB)

(*) Notice: Under 35 U.S.C. 154(b), the term of this patent shall be extended for 0 days.

This patent is subject to a terminal disclaimer.

(21) Appl. No.: 09/238,777

(22) Filed: Jan. 27, 1999

Related U.S. Application Data

(62) Division of application No. 08/884,731, filed on Jun. 30, 1997, now Pat. No. 5,886,215, which is a division of application No. 08/258,167, filed on Jun. 10, 1994, now Pat. No. 5,684,153, which is a continuation-in-part of application No. 08/132,082, filed on Oct. 5, 1993, now abandoned, and application No. 07/918,111, filed on Jul. 20, 1992, now abandoned, said application No. 08/132,082, is a continuation of application No. 07/825,440, filed on Jan. 22, 1992, now Pat. No. 5,250,688, which is a continuation of application No. 07/285,399, filed on Dec. 15, 1988, now abandoned, which is a continuation of application No. 07/777,188, filed on Sep. 18, 1985, now abandoned, said application No. 07/918,111, is a continuation of application No. 07/607,403, filed on Oct. 31, 1990, now abandoned, which is a continuation of application No. 07/085,216, filed on Aug. 12, 1987, now Pat. No. 5,075,455, which is a continuation of application No. 07/641,300, filed on Aug. 16, 1984, now abandoned.

(30) Foreign Application Priority Data

| Aug. 18, 1983 | (GB) | 8322199 |
| Sep. 21, 1983 | (GB) | 8325271 |
| Mar. 30, 1984 | (GB) | 8408322 |
| Sep. 20, 1984 | (GB) | 8423833 |
| Apr. 23, 1985 | (GB) | 8510331 |
| Aug. 16, 1985 | (GB) | 8520618 |

(51) Int. Cl.$^7$ .................. C07D 473/18; C07D 473/32
(52) U.S. Cl. .................................................. 544/277
(58) Field of Search ............................................ 544/277

(56) References Cited

U.S. PATENT DOCUMENTS

| 4,146,715 | 3/1979 | Schaeffer | 544/276 |
| 4,451,478 | 5/1984 | Simon et al. | 424/273 |
| 4,461,757 | 7/1984 | Ogilvie | 424/85 |
| 4,495,190 | 1/1985 | Hagberg et al. | 514/262 |
| 4,579,849 | 4/1986 | MacCoss et al. | 514/262 |
| 4,609,662 | 9/1986 | Krenitsky | 544/277 |
| 4,798,833 | 1/1989 | Johansson et al. | 544/277 |
| 4,845,084 | 7/1989 | Hannah et al. | 514/81 |
| 5,075,445 | * 12/1991 | Jarvest | 544/277 |
| 5,246,937 | 9/1993 | Harnden et al. | 514/261 |
| 5,684,153 | * 11/1997 | Geen | 544/277 |

FOREIGN PATENT DOCUMENTS

| 0 055 23 | 12/1981 | (EP) . |
| 0 055 239 | 6/1982 | (EP) . |
| 0 141 927 | 5/1985 | (EP) . |
| 0 152 316 | 8/1985 | (EP) . |
| 0 186 640 | 7/1986 | (EP) . |
| 352953 | 1/1990 | (EP) . |
| 355986 | 2/1990 | (EP) . |
| 369583 | 5/1990 | (EP) . |
| 404296 | 12/1990 | (EP) . |
| 1 523 865 | 9/1978 | (GB) . |
| 2 104 070 | 3/1983 | (GB) . |
| 2 122 197 | 1/1984 | (GB) . |
| 2 122 198 | 1/1984 | (GB) . |
| 2 130 204 | 5/1984 | (GB) . |
| 2 151 622 | 7/1985 | (GB) . |
| WO 93/23401 | 11/1993 | (WO) . |

OTHER PUBLICATIONS

Geen et al., *Tetrahedron*, 46:19, 6903–6914, 1990.
Chu et al., *J. Heterocylic Chem.*, 23, 289 (1986).
Robins et al., *Can. J. Chem.*, 60 (1982).
Kjellberg et al., *Nucleosides& Nucleotides*, 8:2, 225–256 (1989).
Gillen, Synthesis and properties of Novel Nucleoside and Nucleotide Analogues, Ph.D. Thesis (Apr. 19, 1980).
Pandit et al., Synthetic Communication, 2(6) 345–351 (1972).
Keller et al., Biochem. Pharm. 30(22) 3071–3077 (1981).
Ericson et al., Antimicrobial Agents and Chemotherapy, 27(5), 753–759 (1985).
Ashton et al., J. Med. Chem., 28, 926–933 (1985).
Oberg et al., J. Antimicrob. Chemother., 14(Suppl A), 5–26 (1984).
Grose, PhD. Thesis, Synthesis of Nucleoside Analogues, Univ. of Amersterdam (1971).
Stewart et al., "The Peptides", vol. 3, pp. 172, 180, 181 (1981).
Tippie, et al., Nucleosides & Nucleotide, 3(5), 525–535 (1984).
Smith et al., Antimicrob. Agents Chemotherapy, vol. 22, No. 1, p. 55–61 (Jul. 1982).
Martin et al., J. Med. Chem., vol. 22, pp. 759–761 (1983).
McGee et al., J. Med. Chem., vol. 28, pp. 1242–1245 (1985).
Harnden et al., J. Chem Soc. Perkin Trans., I, pp. 2207–2213 (1989).

* cited by examiner

*Primary Examiner*—Mark L. Berch
(74) *Attorney, Agent, or Firm*—Dara L. Dinner; Stephen Venetianer; Charles M. Kinzig

(57) ABSTRACT

The present invention provides for the compound and synthesis of 9-(4-acetoxy-3-acetoxymethylbutyl)-2-amino-6-chloropurine, which compound is an intermediate involved in the synthesis of penciclovir and famciclovir.

4 Claims, No Drawings

PROCESS FOR THE PREPARATION OF PURINE DERIVATIVES

This application is a divisional of CPA application U.S. Ser. No. 08/884,731, filed Jun. 30, 1997, now U.S. Pat. No. 5,886,215, which is a divisional of U.S. Ser. No. 08/258,167, filed Jun. 10, 1994, now U.S. Pat. No. 5,684,153, which application is a continuation in part application of two U.S. application Ser. Nos., U.S. Ser. No. 08/132,082, filed Oct. 5, 1993 (abandoned), and U.S. Ser. No. 07/918,111, filed Jul. 20, 1992 (abandoned); the application U.S. Ser. No. 08/132,082, filed Oct. 5, 1993 (abandoned), is a continuation of U.S. Ser. No. 07/825,440, filed Jan. 22, 1992, now U.S. Pat. No. 5,250,688, which is a continuation of U.S. Ser. No. 07/285,399, filed Dec. 15, 1988 (abandoned), which is a continuation of U.S. Ser. No. 07/777,188, filed Sep. 18, 1985 (abandoned); the application U.S. Ser. No. 07/918,111, (noted above), filed July 20, 1992 (abandoned) is a continuation of U.S. Ser. No. 07/607,403, filed Oct. 31, 1990 (abandoned) which is a continuation of U.S. Ser. No. 07/085,216, filed Aug. 12, 1987, now U.S. Pat. No. 5,075,455, which is a continuation of U.S. Ser. No. 07/641,300 filed Aug. 16, 1984 (abandoned).

The present invention relates to a process for the preparation of novel compounds, which are of potential use as antiviral agents, to a process for their reparation and to their use as pharmaceuticals.

U.S. Pat. Nos. 5,075,445 and 5,246,937, the subject matter of which is incorporated herein by reference, disclose antiviral compounds penciclovir (Example 4 of '445) and famciclovir (Example 2 of '937) and methods for their preparation. 2-Amino-6-chloropurine (ACP) is 9-substituted with an appropriate side chain precursor, followed by conversion of the 6-chloro moiety to a hydroxy moiety (i.e. to form a guanine) or hydrogen (a 2-aminopurine).

In particular, beginning column 4 of '445, and column 3 of '937, a process is described for the preparation of such purine derivatives wherein the hydroxy groups in the 9-(4-hydroxy-3-hydroxymethylbut-1-yl) substituent are in acylated form, i.e. the ACP is reacted with 2-acyloxymethyl-4-(leaving group)-but-1-yl acylate. The leaving group may be halo, such as chloro, bromo or iodo although alternative leaving groups, such as tosylate or methanesulphonate may be employed. The acyl groups have advantages over the alternative protecting groups already described in acyclonucleoside chemistry in providing a good yield of 9-substitution and avoiding by-products which are difficult to isolate.

The following examples illustrate the process of the invention to form 9-(4-acetoxy-3-acetoxymethylbut-1-yl)-2-amino-6-chloropurine, (DACP). The following descriptions illustrate the preparation of side chain intermediates. Penciclovir is prepared from DACP according to the method described in '445 column 14, lines 4–16 and famciclovir is prepared from DACP according to the method described in Example 2 of '937.

EXAMPLE 1

2-Acetoxymethyl-4-bromobutyl acetate was reacted with ACP as described in Examples 11 and 10 of '445.

EXAMPLE 2

A mixture of ACP (10.0 mmol), 2-acetoxymethyl-4-iodobutyl acetate (3.30 g, 10.5 mmol), and anhydrous potassium carbonate (2.07 g, 15.0 mmol) was stirred for 18 hours at ambient temperature in dry DMF (40 ml) under an atmosphere of dry nitrogen. The mixture was then filtered to remove insoluble material, which was washed well with DMF. The combined filtrates were evaporated under reduced pressure and the residue purified directly by column chromatography on silica gel (150 g), eluting with various dichloromethane-methanol mixtures. Fractions containing the first-eluting N-9 isomer, and the second-eluting N-7 isomer were separately combined, rigorously evaporated and weighed. The N-9:N-7 alkylated product ratio obtained from the isolated weights was checked by integration of the respective H-8 $^1$HNMR signals in the spectrum of the crude residue.

9-(4-Acetoxy-3-acetoxymethylbutyl)-2-amino-6-chloropurine and 7-(4-acetoxy-3-acetoxymethylbutyl)-2-amino-6-chloropurine Column eluant dichloromethane-methanol 25:1.

9-isomer, 75%, m.p. 134–136° (ethyl acetate-diethyl ether).

$^1$HNMR: 1.80–2.05 (m 3H,CHCH$_2$), 2.00 (s,6H,2× COCH$_3$), 4.03 (d,4H,2×CH$_2$O), 4.15 (t,2H,CH$_2$N), 6.87 (brs,2H,NH$_2$), 8.16 (s,1H,H-8).

$^{13}$CNMR: 20.47 (2×CH$_3$), 27.75 (CH$_2$), 34.45 (CH), 40.88 (CH$_2$N), 63.43 (2×CH$_2$O), 123.43 (C-5), 143.07 (C-8), 149.34 (C-6), 154.02 (C-4), 159.68 (C-2), 170.27 (2×CO).

U.V. $\lambda_{max}$ 223.5 ($\epsilon$27.600), 248.5 (5,800), 310 (7,700).

Found; C:47.14, H:4.97, N:19.69. C$_{14}$H$_{18}$N$_5$O$_4$Cl requires; C:47.26, H:5.10, N:19.68%.

7-isomer, 15%, m.p. 159–161° (dec). (butanol).

$^1$HNMR: 1.60–2.10 (m,3H,CHCH$_2$), 2.00 (s,6H,2× COCH$_3$), 4.00 (d,4H,2×CH$_2$O), 4.34 (m,2H,CH$_2$N), 6.56 (brs,2H,NH$_2$), 8.33 (s,1H,H-8).

$^{13}$CNMR: 20.41 (2×CH$_3$), 29.80 (CH$_2$), 34.51 (CH), 44.06 (CH$_2$N), 63.46 (2×CH$_2$O), 114.65 (C-5), 141.97 (C-6), 149.28 (C-8), 159.81 (C-2), 164.24 (C-4), 170.12 (2×CO).

U.V. $\lambda_{max}$ 222.5 ($\epsilon$23.600), 253.5sh (3,700), 323 (5,400)

Found; C:47.31, H:5.17, N:19.88. C$_{14}$H$_{18}$N$_5$O$_4$Cl requires; C:47.26, H:5.10, N:19.68%.

2-Acetoxymethyl-4-bromobutyl acetate was Prepared as Described in Examples 5–8 of '445

2-Acetoxymethyl-4-iodobutyl acetate was prepared as follows:

a) To a stirred solution of 2-(2-benzyloxyethyl)propane-1,3-diol (J. Org. Chem., 1981, 46, 3204) (10.0 g, 47.6 mmol), 4-dimethylaminopyridine (0.55 g, 4.5 mmol), and pyridine (12.3 ml, 0.15 mol) in dichloromethane (54 ml) at −10° C. was added dropwise acetic anhydride (13.2 ml, 0.14 mol) over 20 minutes. After completion of the addition, the reaction mixture was stirred for a further 1 hour at 0° C., then diluted with dichloromethane (100 ml) and washed with 2M hydrochloric acid (2×50 ml), saturated sodium bicarbonate solution (50 ml), and brine (50 ml), dried (MgSO$_4$), and evaporated to give 2-acetoxymethyl-4-benzyloxybutyl acetate as a light yellow oil 13.2 g, 94%). b.p. 160–165°/0.5mm.

$^1$HNMR: 1.62 (q,2H,CHCH$_2$), 2.00 (s,6H,2×CH$_3$), 2.15 (m,1H,CH), 3.51 (t,2H,CH$_2$CH$_2$O), 4.03 (m,4H,2×CH$_2$O), 4.46 (s,2H,OCH$_2$Ph), 7.33 (m,5H,Ph).

$^{13}$CNMR: 20.31 (2×CH$_3$), 27.93 (CHCH$_2$), 34.40 (CH), 63.73 (2×CH$_2$O), 67.22 (CH$_2$CH$_2$O), 71.99 (CH$_2$Ph), 127.22, 127.30, 128.09, 138.54 (Ph), 170.13 (2×CO).

Found; C:65.07, H:7.76. C$_{16}$H$_{22}$O$_5$ requires; C:65.29, H:7.53%.

b) A solution of 2-acetoxymethyl-4-benzyloxybutyl acetate (15.5 g, 52.7 mmol) in ethanol (200 ml) was hydrogenated for 18 hours at ambient temperature over 10% palladium-carbon (2 g). Filtration and evaporation afforded the corresponding alcohol (10.2 g) as a colourless oil.

c) To a stirred solution of the above oil and triethylamine (10.4 ml, 74.8 mmol) in dichloromethane (100 ml) cooled to −5° C. was added a solution of methanesulphonyl chloride (4.6 ml, 59.5 mmol) in dichloromethane (30 ml) dropwise over 30 minutes. After completion of the addition, the reaction mixture was stirred for a further 1 hour at −5° C., then washed with 2M hydrochloric acid (2×100 ml), saturated sodium bicarbonate solution (100 ml), and brine (100 ml), dried (MgSO$_4$) and evaporated to afford the corresponding methanesulphonate (14.1 g) as a pale yellow oil.

d) A mixture of the above oil and sodium iodide (15.0 g, 0.1 mol) was stirred under reflux for 2 hours in acetone (150 ml), then cooled, poured into water (300 ml), and extracted with diethyl ether (3×150 ml). The combined ether extracts were washed with 10% sodium metabisulphite solution (250 ml), and brine (250 ml), dried (MgSO$_4$) and evaporated to give a pale oil. This was purified by flash column chromatography on silica, eluant hexane-diethyl ether 3:2 affording the title compound as a colourless oil (13.1 g, 79% from 2-acetoxymethyl-4-benzyloxybutyl acetate).

$^1$HNMR: 1.88 (q,2H,CH$_2$), 2.02 (s,6H,2×CH$_3$), 2.10 (m,1H,CH), 3.33 (t,2H,CH$_2$I), 4.02 (d,4H,2×CH$_2$O).

$^{13}$CNMR: 5.01 (CH$_2$I), 20.48 (2×CH$_3$), 32.04 (CH$_2$), 37.87 (CH), 62.86 (2×CH$_2$O), 170.02 (2×CO).

EI-MS. m/e: 314 (M$^+$), 254 (M$^+$-HOAc), 211 (M$^+$-HOAcAc), 187 (M$^+$-I).

Found; C:34.56, H:4.99. C$_9$H$_{15}$O$_4$I requires; C:34.42, H:4.81%.

We claim:

1. A process for the preparation of 9-(4-acetoxy-3-acetoxymethylbut-1-yl)-2-amino-6-chloropurine which process comprises the reaction of 2-amino-6-chloropurine with 2-acetoxymethyl-4-(leaving group)-but-1-yl acetate.

2. The process according to claim 1 wherein the leaving group is halo.

3. The process according to claim 2 wherein the leaving group is bromo.

4. The process according to claim 2 wherein the leaving group is iodo.

* * * * *